United States Patent
Lian et al.

(10) Patent No.: US 8,175,709 B2
(45) Date of Patent: May 8, 2012

(54) HEART MONITORING SYSTEM AND METHOD

(75) Inventors: Jie Lian, Beaverton, OR (US); Hannes Kraetschmer, West Linn, OR (US); Dirk Muessig, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 838 days.

(21) Appl. No.: 11/668,491

(22) Filed: Jan. 30, 2007

(65) Prior Publication Data
US 2008/0183088 A1 Jul. 31, 2008

(51) Int. Cl.
*A61N 1/362* (2006.01)

(52) U.S. Cl. .......................................... 607/30; 600/510

(58) Field of Classification Search .................. 607/9, 30; 600/509, 510
See application file for complete search history.

(56) References Cited

U.S. PATENT DOCUMENTS

| | | | |
|---|---|---|---|
| 5,265,602 A | 11/1993 | Anderson et al. | |
| 5,331,966 A | 7/1994 | Bennett et al. | |
| 5,740,811 A | 4/1998 | Hedberg et al. | |
| 6,505,067 B1 | 1/2003 | Lee et al. | |
| 6,512,940 B1 | 1/2003 | Brabec et al. | |
| 6,522,915 B1 | 2/2003 | Ceballos et al. | |
| 6,564,106 B2 | 5/2003 | Guck et al. | |
| 6,631,290 B1 | 10/2003 | Guck et al. | |
| 6,633,776 B2 * | 10/2003 | Levine et al. | 600/523 |
| 6,658,283 B1 | 12/2003 | Bornzin et al. | |
| 6,813,514 B1 * | 11/2004 | Kroll et al. | 600/509 |

OTHER PUBLICATIONS

Filter definition page from Longman Dictionary of Contemporary English. http://www.Idoceonline.com/Technology-topic/filter_1 Accessed Nov. 9, 2009.*

* cited by examiner

*Primary Examiner* — George Evanisko
(74) *Attorney, Agent, or Firm* — ARC IP Law, PC; Joseph J. Mayo (57) ABSTRACT

A system for heart monitoring comprises an IEGM input for an intracardiac electrocardiogram (IEGM) that is connected to an active filtering stage that is adapted to transform an incoming IEGM into an output ECG signal. The active filtering stage is connected to a filter characterization stage that is adapted to process a recorded, patient specific IEGM template and a corresponding SECG template and to adapt the filter characteristics of said active filtering stage such that the filter characteristics best characterize the input-output relationship between the IEGM template and the corresponding SECG template. As a consequence, the active filtering stage is adapted to transform an incoming IEGM such that the output ECG signal closely resembles a morphology of a corresponding SECG.

5 Claims, 9 Drawing Sheets

HEART MONITORING SYSTEM AND METHOD

BACKGROUND OF THE INVENTION

1. Field of the Invention

The invention relates to a system for heart monitoring and a method for heart monitoring. The system comprises an implantable medical device adapted to pick up in intracardiac electrocardiogram and an external device adapted to wirelessly communicate with the implantable medical device. The method includes a step of acquiring an intracardiac electrocardiogram and a step of processing the intracardiac electrocardiogram. More particularly, the invention refers to a system and a method for generating a surface electrocardiogram (SECG) from an intracardiac electrocardiogram (IEGM).

2. Description of the Related Art

During pacemaker or ICD follow-up, a surface ECG (SECG) is routinely measured to examine the status of the electrical conduction system of the heart, and to confirm the normal functionality of the implant device, for instance, to verify pacing capture control and ensure proper arrhythmia detection. However, measuring SECG is associated with several drawbacks. First, it increases the duration of the follow-up time and adds to the overall cost. Second, skin preparation and electrode handling may bring considerable inconvenience to the patient, particularly for the females. Third, from one follow-up session to another, the electrodes may not be placed at the exact same locations on the patient, thus resulting in somewhat different SECG. Fourth, externally attached electrodes are subject to motion artifacts from postural changes and the relative displacement between the skin and the electrodes. Finally, the SECG is known to be susceptible to interference such as muscle noise, power line interference, baseline drift from respiration or motion, etc.

Therefore, there is a need to provide the implant device Lead-Free ECG feature, that is, to provide a means to generate a SECG-like output ECG signal without the need for attaching the skin electrodes to the patients.

One method for Lead-Free ECG is based on subcutaneous electrodes or subcutaneous electrode array (SEA). For example, U.S. Pat. No. 5,331,966 issued to Bennett et al. discloses a method and apparatus for providing SECG-like signals via an array of relatively closely spaced subcutaneous electrodes located on the body of an implanted device. In a typical embodiment, an array of three electrodes disposed orthogonally on the surface of the pulse generator and connector block and facing outwardly towards the patient's skin is employed to develop the far-field IEGM signal comprising the P-QRS-T signals that are similar to the SECG.

Several patents were issued to further improve the design of the SEA. For example, U.S. Pat. No. 6,522,915 discloses an alternate method and apparatus for detecting electrical cardiac signals via a SEA located on a shroud circumferentially placed on the perimeter of an implanted pacemaker. U.S. Pat. No. 6,512,940 by Brabec et al. discloses the use of a spiral electrode using in conjunction with the shroud described in the Ceballos et al. disclosure. In addition, U.S. Pat. Nos. 6,564,106 and 6,631,290, both issued to Guck and Donders, discloses the use of sensing electrodes placed into recesses incorporated along and into the peripheral edge of the implantable pacemaker.

Furthermore, U.S. Pat. No. 6,505,067 issued to Lee et al. discloses a system and method for deriving a virtual SECG based on the signals recorded by the SEA. The SEA comprises at least three (preferably 3 or 4) subcutaneous electrodes located on the surface of the implant device. The signals recorded between these electrodes form independent directional vectors. The method used to determine the virtual SECG is based on vector arithmetic principles.

Although the far-field IEGM recorded by the SEA may approximate the SECG, the disadvantage is the need for special design, fabrication, and manufacture of the SEA and the associated circuits, which add to the hardware complexity.

A different approach for Lead-Free ECG is based on far-field IEGM recorded by existing implant device and their lead system. For example, U.S. Pat. No. 5,265,602 issued to Anderson et al. discloses a pacemaker, which has a special sense configuration that records the IEGM between the RA ring and the RV ring electrodes. The 'RA ring-RV ring' far-field IEGM is relatively unaffected by the after-potentials and polarization effects, but its morphology is generally quite different from SECG.

Similar approach is disclosed in U.S. Pat. No. 6,658,283 issued to Bornzin et al. According to this disclosure, far-field IEGM is recorded from various lead configurations between widely spaced electrodes including RA tip, RV tip, RA ring, RV ring, and case (including the 'RA ring-RV ring' configuration). The recorded far-field IEGM is further processed by a cascade of linear filters with designed output frequency bands to generate the Lead-Free ECG, which may not be satisfactory in terms of signal amplitude and morphology.

Another approach is disclosed in U.S. Pat. No. 5,740,811 issued to Hedberg et al. This patent also discloses multiple lead configurations for measuring the far-field IEGM. One or more channels of the far-field IEGM are first pre-processed (amplified, filtered, blocked, transferred), then post-processed by a pre-trained artificial neural network or fuzzy logic to generate the Lead-Free ECG. However, the artificial neural network or fuzzy logic trained from one dataset may not be applicable to another dataset.

U.S. Pat. No. 6,813,514 issued to Kroll et al. discloses a method to emulate the multi-lead SECG by solving the forward problem. Each channel of SECG or IEGM is converted into a time-varying vector. The SECG matrix (containing multiple SECG vectors) is linearly linked to the IEGM matrix (containing multiple IEGM vectors) by a transfer matrix, which can be pre-calculated by solving the inverse problem. However, this method requires multi-channel IEGM recordings. Moreover, calibration of different transfer matrices is needed to account for different factors affecting the relative locations of the internal leads, such as respiration and posture.

In view of the forgoing descriptions, the present invention provides an advanced Lead-free ECG method and apparatus. In this disclosure, the following terms are used:

| Term | Description |
| --- | --- |
| AEGM | Atrial electrogram |
| AP | Atrial pace event = effective atrial stimulation pulse |
| $A_{rs}$ | atrial refractory sense event |
| AS | Atrial sense event |
| AV | Atrial-ventricular (or atrioventricular) |
| ICD | Implantable cardioverter-defibrillator |
| IEGM | Intracardiac electrogram |
| NLMS | Normalized least mean square |
| PVARP | post ventricular atrial refractory period |
| RA | Right atrium |
| RV | Right ventricle |
| SEA | Subcutaneous electrode array |
| SECG | Surface electrocardiogram |
| SVC | Superior vena cava |
| VEGM | Ventricular electrogram |
| VP | Ventricular pace event = effective ventricular stimulation pulse |
| VS | Ventricular sense event |

BRIEF SUMMARY OF THE INVENTION

It is an object of the invention to provide an improved approach for obtaining a SECG.

According to the invention, this object is achieved by a system for heart monitoring comprising an IEGM input for an intracardiac electrocardiogram (IEGM) that is connected to an active filtering stage that is adapted to transform an incoming IEGM into an output ECG signal, wherein the active filtering stage is connected to a filter characterization stage that is adapted to process a recorded, patient specific IEGM template and a corresponding SECG template and to adapted the filter characteristics of said active filtering stage such that the filter characteristics best characterize the input-output relationship between the IEGM template and the corresponding SECG template and, as a consequence, the active filtering stage is adapted to transform an incoming IEGM such that the output ECG signal closely resembles a morphology of a corresponding SECG.

The active filtering stage may comprise a plurality of filters wherein each filter is characterized by an individual set of filter coefficients. In particular it is preferred that the filtering stage comprises an AS filter for filtering atrial IEGM templates corresponding an atrial sense event, an AP filter for filtering atrial IEGM templates corresponding an atrial pace event, a VS filter for filtering ventricular IEGM templates corresponding a ventricular sense event and a VP filter for filtering ventricular IEGM templates corresponding a ventricular pace event.

The filter characterization stage preferably is adapted to determine the difference between the SECG template and the output signal and to iteratively determine those filter characteristics that lead to least mean squares of said difference. This corresponds to a normalized least mean square method of filter adaptation. An alternative approach could be based on recursive least squares.

It is further preferred that the filter characterization stage is adapted to match pairs of IEGM and SECG templates based on fiducial points.

In a preferred embodiment the system is adapted to generate marker signals corresponding to the occurrence of atrial and/or ventricular events. The filter characterization stage preferably comprises an marker input for such marker signal and wherein the filter characterization stage is adapted to determine said fiducial based on said marker signal.

The object of the invention is also achieved by a method of transforming an incoming intracardiac electrogram (IEGM) into an output ECG signal, that comprises the steps of:

Acquisition of at least one patient specific intracardiac electrogram (IEGM) template and at least one corresponding surface electrocardiogram (SECG) template, Determination of filter characteristics that best characterize the input-output relationship between said IEGM template and said corresponding SECG template, and Adjustment of an active filtering stage such that the active filtering stage exhibits the filter characteristics thus determined.

Preferably, the step of determination of filter characteristics comprises determining an error vector that reflects the difference between the SECG template and the output signal and iteratively determining those filter characteristics that lead to least mean squares of said error vector.

It is further preferred, if the step of acquisition comprises acquiring separate IEGM templates corresponding to an intraatrial electrocardiogram (AEGM) and an intraventricular electrocardiogram (VEGM). Such AEGM is obtained by means of an atrial sensing stage connected to at least one electrode in an atrium of a heart whereas such VEGM is obtained by means of a ventricular sensing stage connected to at least one electrode in a ventricle of a heart. In a further preferred embodiment, the step of acquisition comprises acquiring separate IEGM templates corresponding to paced events and to sense events. A paced event can either be an atrial pace event AP or a ventricular pace event VP. Similarly, a sense event can either be an atrial sense event AS or a ventricular sense VS. A sense event corresponds to a natural (intrinsic) excitation of a corresponding heart chamber and paced event is a stimulated excitation of a corresponding heart chamber induced by a stimulation pulse delivered the implantable medical device.

Preferably, the method comprises determination of two or more different filter characteristics for IEGM signals of different origin, atrium or ventricle, and/or for events of different nature, that is paced or sensed.

The step of determination of filter characteristics preferably comprises a first step of template matching wherein a pair of IEGM and SECG templates are matched based on fiducial points. In a further preferred embodiment the step of template matching comprises determination of fiducial points based on a marker signal, said marker signal being generated upon detection of a ventricular or an atrial event.

It is to be appreciated that features of preferred embodiments of the invention may be combined in any useful manner thus arriving a further preferred embodiments of the invention not explicitly mentioned in this disclosure.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
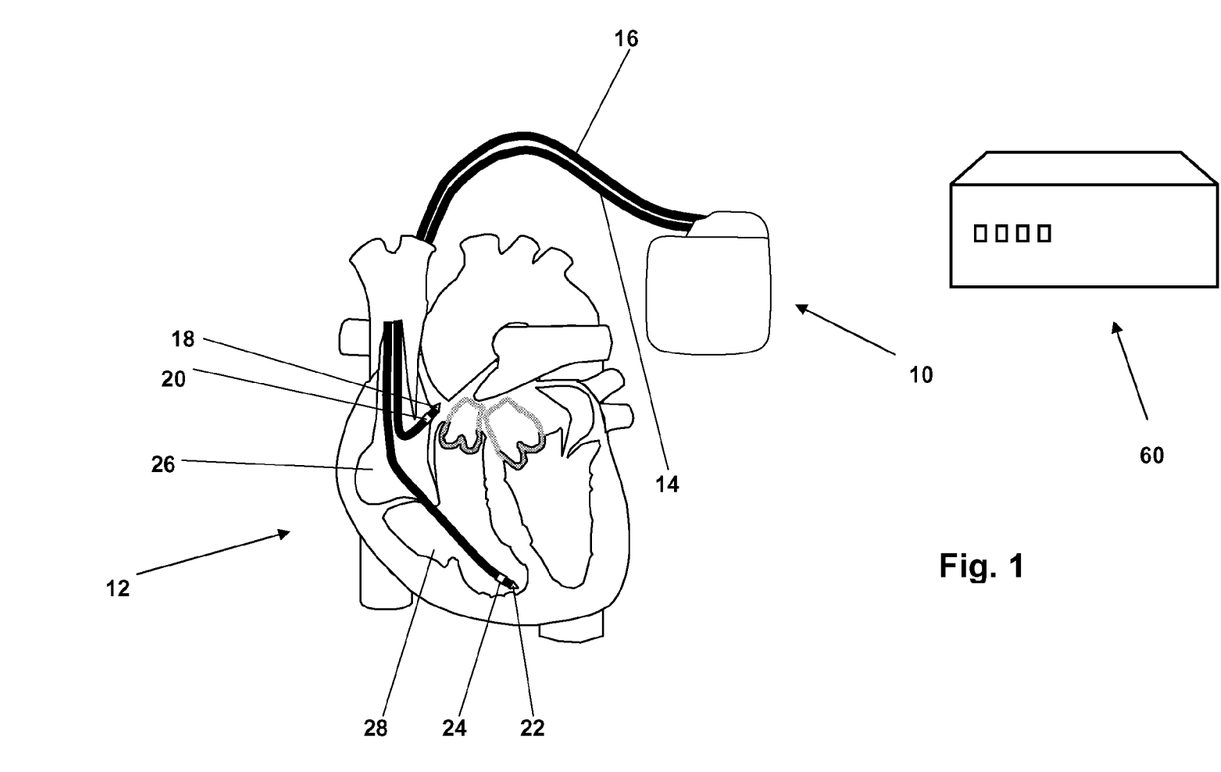
FIG. 1 shows a heart monitoring system comprising an implantable dual chamber pacemaker connected to leads placed in a heart and an external device.

In FIG. 1 a heart monitoring system comprising an implantable medical device 10 and an external device 60. The implantable medical device is an implantable dual chamber pacemaker.

The dual chamber pacemaker 10 is connected to pacing/sensing leads placed in a heart 12 is illustrated. The pacemaker 10 is electrically coupled to heart 12 by way of leads 14 and 16. Lead 14 has a pair of right atrial electrodes 18 and 20 that are in contact with the right atria 26 of the heart 12. Lead 16 has a pair of electrodes 22 and 24 that are in contact with the right ventricle 28 of heart 12 and an atrial cardioversion shock coil placed in atrium 26 of heart 12. Electrodes 18 and 22 are tip-electrodes at the very distal end of leads 14 and 16, respectively. Electrode 18 is a right atrial tip electrode RA-Tip and electrode 22 is a right ventricular tip electrode. Electrodes 20 and 24 are ring electrodes in close proximity but electrically isolated from the respective tip electrodes 18 and 22. Electrode 20 forms a right atrial ring electrode RA-Ring and electrode 24 forms a right ventricular ring electrode RV-Ring. Atrial cardioversion shock coil is coil electrode providing a relatively large geometric area when compared to the stimulation electrodes 18, 20, 22 and 24.

In alternative embodiments, a part of the pacemaker's 10 housing may form a case electrode that can be connected to a ventricular sensing stage or an atrial sensing stage or both, see below. Furthermore, one or more coil electrodes for delivering defibrillation pulses can be provided on the ventricular lead 16 or the atrial lead 14. For ventricular defibrillation a ventricular coil electrode would be provided on the ventricular electrode lead 16 for placement in the right ventricle 28. Likewise, a superior vena cava electrode could be provided on the atrial electrode lead 14 or the ventricular electrode lead 16. By means of such coil electrodes pacemaker 10 could act as an implantable cardioverter/defibrillator.

Figure 2:
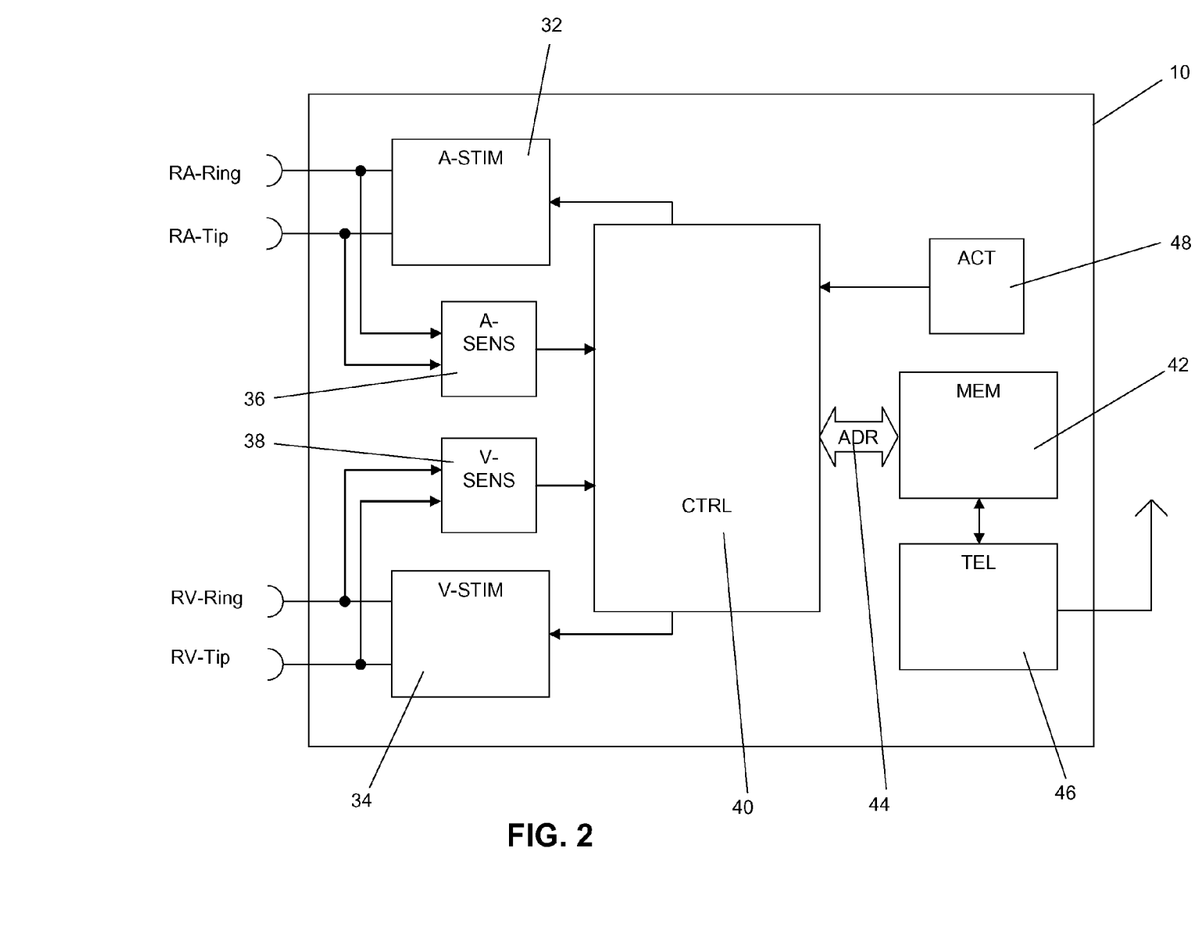
FIG. 2 is a block diagram of the implantable pacemaker of FIG. 1.

Referring to FIG. 2 a simplified block diagram of a dual chamber pacemaker 10 is illustrated. During operation of the pacemaker leads 14 and 16 are connected to respective output/input terminals of pacemaker 10 as indicated in FIG. 1 and carry stimulating pulses to the tip electrodes 18 and 22 from an atrial stimulation pulse generator A-STIM 32 and a ventricular pulse generator V-STIM 34, respectively. Further, electrical signals from the atrium are carried from the electrode pair 18 and 22, through the lead 14, to the input terminal of an atrial channel sensing stage A-SENS 36; and electrical signals from the ventricles are carried from the electrode pair 22 and 24, through the lead 16, to the input terminal of a ventricular sensing stage V-SENS 38.

Controlling the dual chamber pacer 10 is a control unit CTRL 40 that is connected to sensing stages A-SENS 36 and V-SENS 38 and to stimulation pulse generators A-STIM 32 and V-STIM 34. Control unit CTRL 40 receives the output signals from the atrial sensing stage A-SENS 36 and from the ventricular sensing stage V-SENS 38. The output signals of sensing stages A-SENS 36 and V-SENS 38 are generated each time that a P-wave representing an intrinsic atrial event or an R-wave representing an intrinsic ventricular event, respectively, is sensed within the heart 12. An As-signal is generated, when the atrial sensing stage A-SENS 36 detects a P-wave and a Vs-signal is generated, when the ventricular sensing stage V-SENS 38 detects an R-wave.

Control unit CTRL 40 also generates trigger signals that are sent to the atrial stimulation pulse generator A-STIM 32 and the ventricular stimulation pulse generator V-STIM 34, respectively. These trigger signals are generated each time that a stimulation pulse is to be generated by the respective pulse generator A-STIM 32 or V-STIM 34. The atrial trigger signal is referred to simply as the "A-pulse", and the ventricular trigger signal is referred to as the "V-pulse". During the time that either an atrial stimulation pulse or ventricular stimulation pulse is being delivered to the heart, the corresponding sensing stage, A-SENS 36 and/or V-SENS 38, is typically disabled by way of a blanking signal presented to these amplifiers from the control unit CTRL 40, respectively.

This blanking action prevents the sensing stages A-SENS 36 and V-SENS 38 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Furthermore, atrial sense events As recorded shortly after delivery of a ventricular stimulation pulses during a preset time interval called post ventricular atrial refractory period (PVARP) are generally recorded as atrial refractory sense event Ars but ignored.

Control unit CTRL 40 comprises circuitry for timing ventricular and/or atrial stimulation pulses according to an adequate stimulation rate that can be adapted to a patient's hemodynamic need as pointed out below.

Still referring to FIG. 2, the pacer 10 includes a memory circuit MEM 42 that is coupled to the control unit CTRL 40 over a suitable data/address bus ADR 44. This memory circuit MEM 42 allows certain control parameters, used by the control unit CTRL 40 in controlling the operation of the pacemaker 10, to be programmably stored and modified, as required, in order to customize the pacemaker's operation to suit the needs of a particular patient. Such data includes the basic timing intervals used during operation of the pacemaker 10 and AV delay values and hysteresis AV delay values in particular.

Further, data sensed during the operation of the pacemaker may be stored in the memory MEM 42 for later retrieval and analysis. This includes atrioventricular interval data that are acquired by the control unit CTRL 40. Control unit CTRL 40 is adapted to determine the atrioventricular interval data as required for automatic atrioventricular interval analysis by determining the time interval between an atrial event, either sensed (As) or stimulated (Ap) and an immediately following ventricular sensed event Vs as indicated by the ventricular sensing stage V-SENS 38.

A telemetry circuit TEL 46 is further included in the pacemaker 10. This telemetry circuit TEL 46 is connected to the control unit CTRL 40 by way of a suitable command/data bus. Telemetry circuit TEL 46 allows for wireless data exchange between the pacemaker 10 and some remote programming or analyzing device which can be part of a centralized service center serving multiple pacemakers.

The pacemaker 10 in FIG. 1 is referred to as a dual chamber pacemaker because it interfaces with both the right atrium 26 and the right ventricle 28 of the heart 12. Those portions of the pacemaker 10 that interface with the right atrium, e.g., the lead 14, the P-wave sensing stage A-SENS 36, the atrial stimulation pulse generator A-STIM 32 and corresponding portions of the control unit CTRL 40, are commonly referred to as the atrial channel. Similarly, those portions of the pacemaker 10 that interface with the right ventricle 34, e.g., the lead 16, the R-wave sensing stage V-SENS 38, the ventricular stimulation pulse generator V-STIM 34, and corresponding portions of the control unit CTRL 40, are commonly referred to as the ventricular channel.

In order to allow rate adaptive pacing in a DDDR or a DDIR mode, the pacemaker 10 further includes a physiological sensor ACT 48 that is connected to the control unit CTRL 40 of the pacemaker 10. While this sensor ACT 48 is illustrated in FIG. 2 as being included within the pacemaker 10, it is to be understood that the sensor may also be external to the pacemaker 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

As is obvious from the above, the atrial sensing stage A-SENS 36 and the ventricular sensing stage V-SENS 38 are adapted to pick up an atrial intracardiac electrocardiogram (AEGM) and a ventricular intracardiac electrocardiogram (VEGM), respectively. These EGMs are fed to control unit CTRL 40 for further processing. Either the ventricular sensing stage V-SENS 38 or control unit CTRL 40 is adapted to generate a ventricular marker signal each time a ventricular vent—either sensed or paced—occurs. Thus, a ventricular marker channel is established providing timing information on ventricular events. In a similar manner, an atrial marker channel can be established for deriving atrial marker signals from the AEGM and thus providing timing information on atrial events.

The AEGM, the VEGM and the ventricular marker signals are fed from the respective sensing stages 36 and 38 via control unit CTRL 40 and memory MEM 42 to telemetry unit TEL 46 and thus can be wirelessly transmitted to an external device 60 in the proximity of pacemaker 10.

Preferably, the AEGM and VEGM signals are data-compressed in order to save bandwidth for transmission of the IEGMs.

Figure 3:
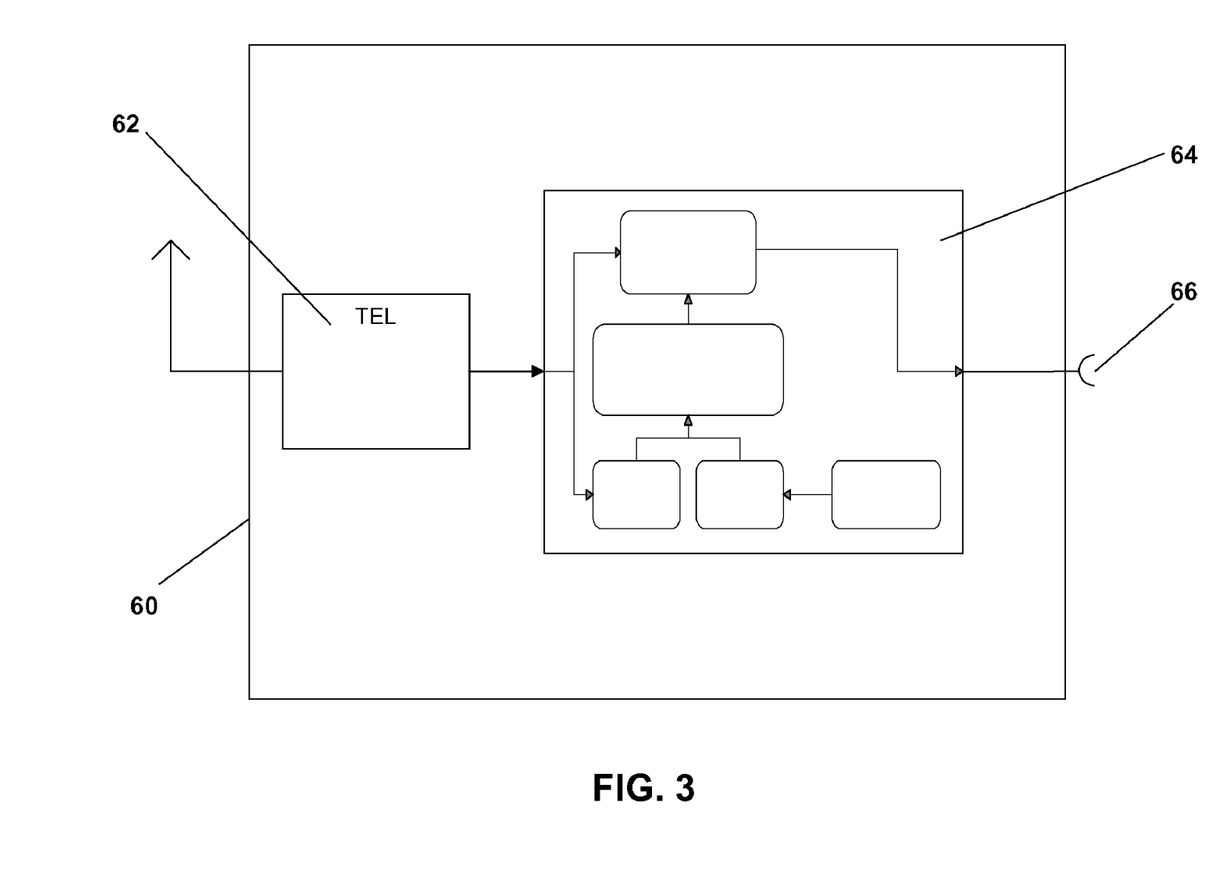
FIG. 3 is a block diagram of the external device of FIG. 1.

The external device 60 is further illustrated in FIG. 3. A telemetry unit 62 for receiving data from and transmitting data to the implantable device (pacemaker 10). As the data received from pacemaker 10 may be compressed, external device telemetry unit 62 may comprise a data decompressing stage. Connected to telemetry unit 62 is an adaptive filter unit 64 that is illustrated in further detail hereinafter. Adaptive filter unit 64 is adapted to transform an IEGM signal received from pacemaker 10 via telemetry unit 62 into an output ECG signal closely resembling a SECG. In order to feed the output ECG signal to a device for displaying the output ECG signal, an output terminal 66 is provided and connected to the adaptive filter unit 64.

The external device 60 can be a programmer or a bedside device comprising further features not illustrated here.

Figure 4:
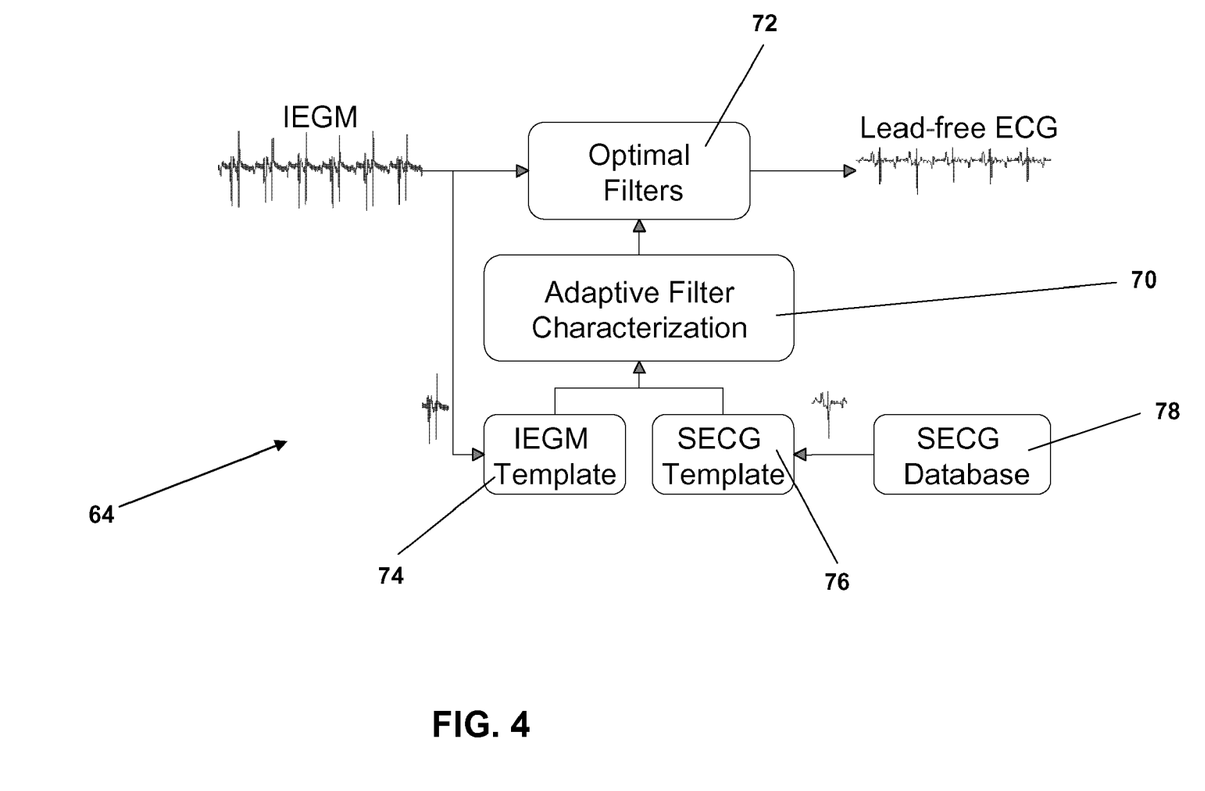
FIG. 4 shows the schematic diagram of the adaptive filter approach for obtaining a SECG from an IEGM.

Refer to FIG. 4. The adaptive filter unit 64 comprises two stages: a filter characterization stage 70 and an active filtering stage 72. The filter characterization stage is inactive when the active filtering stage is adapted or updated. Thereafter, the active filtering stage operates on its own and processes an incoming IEGM to generate an output ECG corresponding to a SECG. The filter characterization stage 70 thus performs the method steps of filter characterization whereas the active filtering stage 72 performs a transformation of an incoming IEGM into an output ECG by way of filtering.

During filter characterization, the filter characterization stage 70 takes representative beats of IEGM (IEGM templates) and the desired beats of SECG (SECG templates) as input. The IEGM templates and the SECG templates are generated by an IEGM template generator 74 and a SECG template generator 76, respectively. The IEGM template generator 74 is adapted to generate an IEGM template corresponding to a typical morphology of an IEGM during one heart cycle. The SECG template generator 76 is adapted to retrieve an SECG template from a SECG database 78 that corresponds to the physiological conditions under which the IEGM template was generated.

By using adaptive filter technique, the filter characterization stage 70 determines optimal filter coefficients that best characterize the input-output relationship between the IEGM and the SECG templates thus adjusting the active filtering stage 72. Preferably, the filter characterization and adjustment of the active filtering stage 72 is done after initial device implant. Alternatively, it could be repeated (updated) during routine follow-up if necessary.

After the active filtering stage 72 is characterized (adjusted or updated), the previously characterized filters of the active filtering stage 72 actively filter the input IEGM signals to generate the output ECG signal. In a typical embodiment, the active filtering occurs during device follow-up or is performed in the remote service centre. In another embodiment, the active filtering is processed inside the device. The synthesized output ECG is then transmitted via telemetry to the programmer for display, or transmitted to the remote service centre through Home Monitoring technology.

The IEGM templates are wide-band signals provided by the sensing channels that include sensing stages 36 and 38. Because the filter characteristics could be substantially different for sensed events and paced events, these IEGM templates should be representative (for example, by taking multiple-beat average) of at least four different event types: atrial sense (AS), ventricular sense (VS), atrial pace (AP), and ventricular pace (VP).

The SECG templates provide waveforms that are representative of sensed P wave, sensed R wave, paced P wave, and paced R wave from desired surface lead. These SECG templates could be selected from an external SECG database (generic ECG), or could be obtained from the same patient (subject-specific) if it is available.

In one embodiment, the patient-specific IEGM templates are stored in the memory MEM 42 of the implant device (pacemaker 10) and the generic SECG templates are stored in the programmer (external device 60) or remote service centre. In another embodiment, the SECG templates are stored in the device memory if they are patient-specific.

In a preferred embodiment, the normalized least mean square (NLMS) method is used to characterize the optimal filter coefficients relating the IEGM and SECG, by minimizing the error vector between the filter output signal (estimated SECG template) and desired (that is: stored) SECG templates. However, as known in the art, other types of adaptive filters e.g. based on recursive least squares, can also be used to achieve the same goal. Different filters (AS filters, VS filters, AP filters, and VP filters) are determined for sensed beats and paced beats from atrial and ventricle origins, respectively. In addition, the filters for each event type (AS, VS, AP, VP) contain a bank of filters, whose characteristics (coefficients) vary from sample to sample, to account for the non-stationary properties of the cardiac signals.

In a typical embodiment, the external device 60 (programmer or remote service centre) interrogates the implant device (pacemaker 10) to obtain the IEGM templates, and also retrieves the SECG templates from the external device's SECG database 78. The external device 60 then runs the NLMS algorithm to characterize the active filtering stage 72 by determining the optimal filter coefficients that best relate the IEGM templates to the SECG templates. The calculated optimal filter coefficients are then saved in the external device 60 and used in later active filtering.

In another embodiment, the calculated optimal filter coefficients are stored in the implant device 10, so that the implant device 10 can use them for active filtering and generate the output ECG signal.

To synthesize SECG containing P-QRS-T waves, the information pertaining to atrial and ventricular events must be present in the input IEGM channel(s). Depending on the choice of input IEGM channels, there are at least three different adaptive filter methods.

The first is the single channel NLMS approach that takes the far-field AEGM (obtained by means of an atrial sensing stage that is either connected to right atrial ring electrode RA RING and the housing (case) of pacemaker 10 or to superior vena cava coil electrode SVC COIL and the housing (case) of pacemaker 10) as input to generate the output ECG signal. The far-field AEGM is the composite signal that reflects both local atrial activity and far-field ventricular activity. Through filter characterization, two sets of filter coefficients are obtained to project the far-field AEGM to the output ECG, with one filter set dedicated to local atrial signal, and another filter set dedicated to far-field ventricular signal.

The second is the dual-channel NLMS approach that takes both far-field AEGM (by means of an atrial sensing stage that is either connected to right atrial ring electrode RA RING and the housing (case) of pacemaker 10 or to superior vena cava coil electrode SVC COIL and the housing (case) of pacemaker 10) and VEGM (by means of a ventricular sensing stage that is either connected to right ventricular ring electrode RV RING and the housing (case) of pacemaker 10 or a right ventricular coil electrode RV COIL and the housing (case) of pacemaker 10 or to the RV tip electrode 22 and RV ring electrode 24, as depicted in FIGS. 1 and 2) as inputs. Through filter characterization, the dual-channel NLMS algorithm simultaneously determines both atrial and ventricular filter coefficients for a ventricular active filtering stage and an atrial active filtering stage. The output ECG signal is formed as the sum of the filtered AEGM and the filtered VEGM.

The third is the independent two-single-channel NLMS approach. Similar to the dual-channel NLMS approach, it takes far-field AEGM (by means of an atrial sensing stage that is either connected to right atrial ring electrode RA RING and the housing (case) of pace-maker 10 or to superior vena cava coil electrode SVC COIL and the housing (case) of pace-maker 10) and VEGM (by means of a ventricular sensing stage that is either connected to right ventricular ring electrode RV RING and the housing (case) of pacemaker 10 or a right ventricular coil electrode RV COIL and the housing (case) of pacemaker 10 or to the RV tip electrode 22 and RV ring electrode 24, as depicted in FIGS. 1 and 2) as input. The output ECG signal is formed as the sum of the filtered AEGM and the filtered VEGM. However, in this approach, atrial filters and ventricular filters are determined independently through single-channel NLMS method. Specifically, one NLMS process determines the atrial filter coefficients (relating AEGM to P wave), and a separate NLMS process determines the ventricular filter coefficients (relating VEGM to QRS-T waves).

The following descriptions and examples are based on the third embodiment of the invention that features independent two-single-channel NLMS, although it should be understood that the same principles apply to the other two approaches described above as well.

Figure 5:
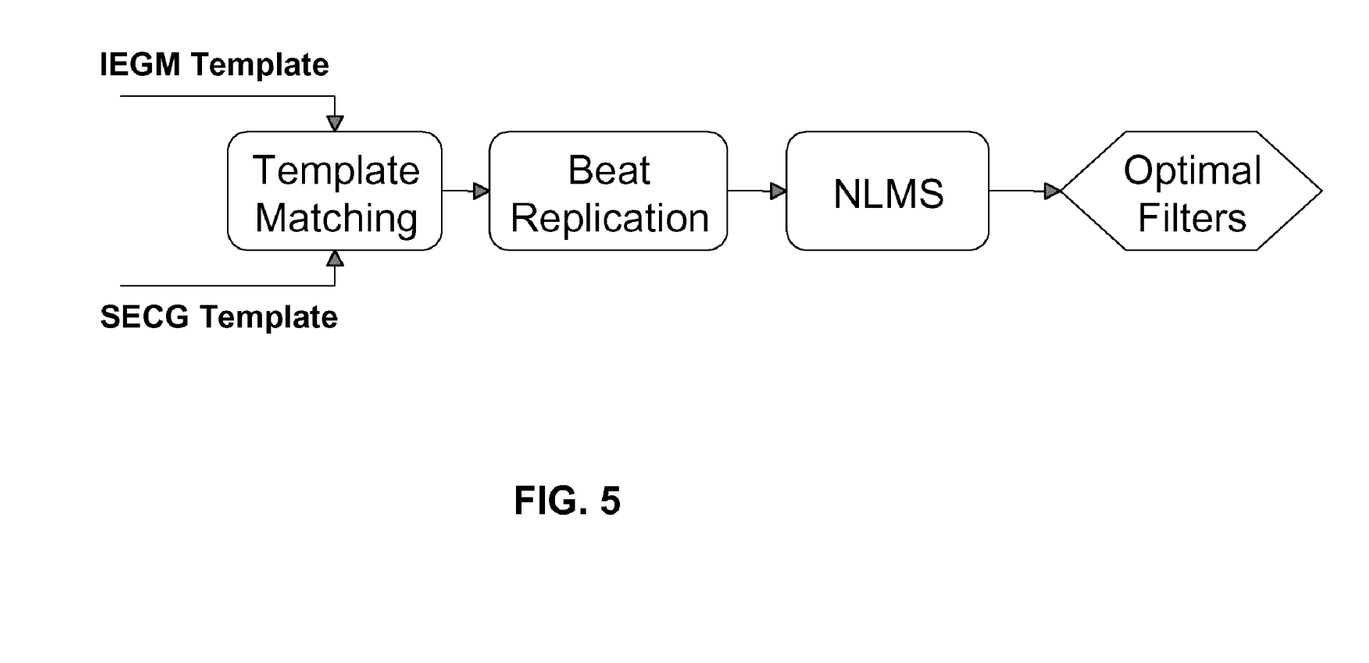
FIG. 5 shows the block diagram of the processes involved in filter characterization stage.

Refer to FIG. 5. According to this embodiment, input IEGM template and corresponding SECG template are matched based on respective fiducial points, replicated if necessary, then fed into the NLMS algorithm to generate the optimal filters. In a preferred embodiment, four sets of optimal filter coefficients are characterized based on four pairs of input templates: (1) AS filter coefficients (derived from AEGM template of AS event and SECG template of sensed P wave); (2) VS filter coefficients (derived from VEGM template of VS event and SEGM template of sensed QRS-T waves); (3) AP filter coefficients (derived from AEGM template of AP event and SECG template of paced P wave); (4) VP filter coefficients (derived from VEGM template of VP event and SECG template of paced QRS-T waves).

When applied to a corresponding filtering stage, the filter coefficients form a corresponding AS filter, VS filter, AP filter and VP filter, respectively.

Figure 6:
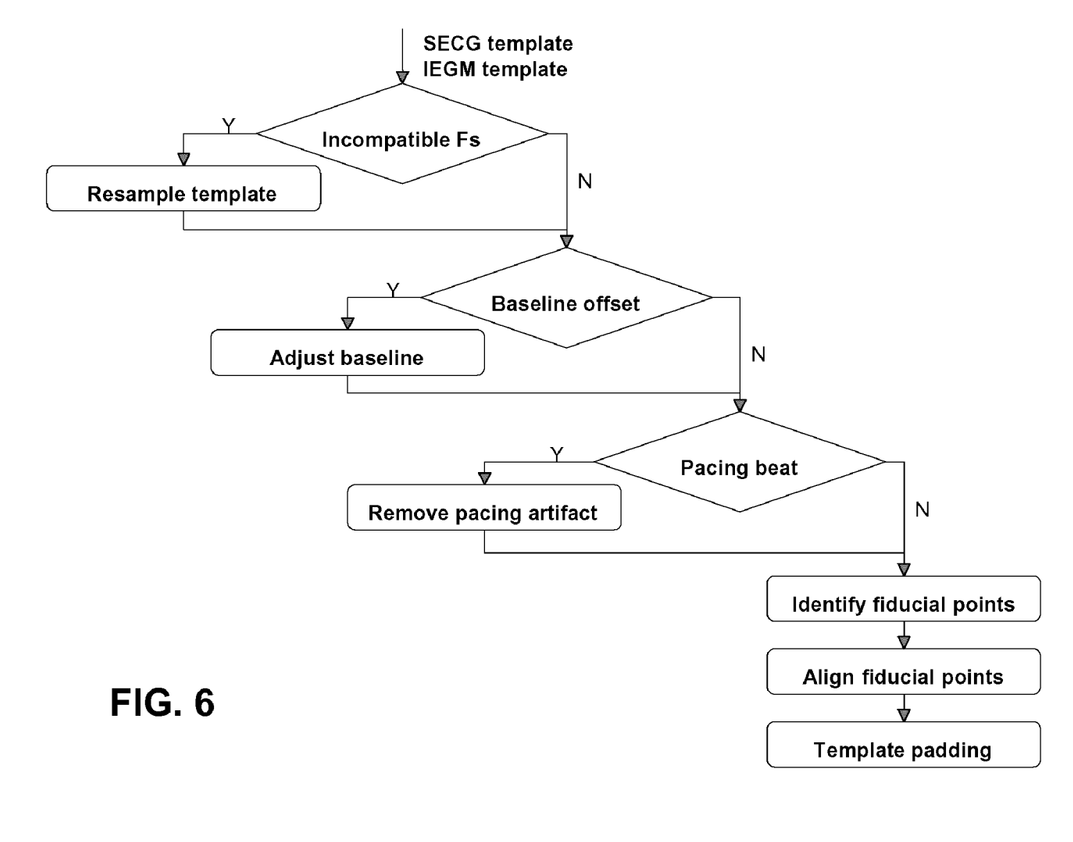
FIG. 6 shows the schematic flowchart for the template matching.

Refer to FIG. 6. Template matching takes a pair of IEGM and SECG templates and matches them based on fiducial points. The following summarizes the steps involved in template matching.

Resample SECG template if necessary to ensure it has the same sampling frequency as the IEGM template. In a preferred embodiment, both templates have fixed sampling frequency (e.g., 256 Hz or 512 Hz).

Adjust baseline of IEGM and SECG templates if necessary to remove DC offset. In a preferred embodiment, the predefined SECG template should already have baseline adjusted. The IEGM template, which is obtained from the device through multi-beat averaging, also should be high-pass filtered and free of baseline offset.

Remove pacing artifacts from the templates if necessary. In a preferred embodiment, the predefined paced SECG templates should already be pre-edited to remove the pacing spike. The paced IEGM templates should also be artifact-free because of the analog and digital blanking after the pace.

Identify the fiducial points of the IEGM and SECG templates. In a preferred embodiment, the fiducial point for SECG template, regardless of pacing or sensing, is defined by its peak, that is, the peak of P wave (for P wave template), and the peak of R wave (for the QRS-T template). For paced IEGM, the device-provided pace marker identifies the fiducial point. For sensed IEGM, the nearest peak (either positive or negative) following (or around) the sense marker (e.g., in a 20 ms window) is considered as the fiducial point.

For sensed event, the SECG fiducial point is aligned with corresponding IEGM fiducial point with a programmable delay (default 30 ms) to account for the phase delay between IEGM and SECG. For paced event, an additional delay (default 20 ms) is added to account for the interval from pace marker to the peak of evoked potential in IEGM. Optionally, if the T wave peaks can be identified in both SECG and VEGM templates, they can also be aligned with proper delay (default 30 ms).

After alignment of the fiducial points, the IEGM and SECG templates are adjusted to the same length. This can be done by pre-padding the first sample of the shorter pre-fiducial segment, and post-padding the last sample of the shorter post-fiducial segment. If the T wave peaks are also aligned, then partial RT segment of the SECG template (e.g., 100 ms after R peak to 30 ms before T peak) is re-sampled to match the segment length of the corresponding IEGM template.

According to this invention, beat replication is an optional step that replicates the aligned IEGM and SECG templates to multiple cycles. The purpose of beat replication is to generate longer training data for the input of adaptive filters. For a stationary signal, the longer the training set, the more stable the filter will converge. However, for non-stationary cardiac signal, the filters may be characterized after a single beat adaptation.

Figure 7:
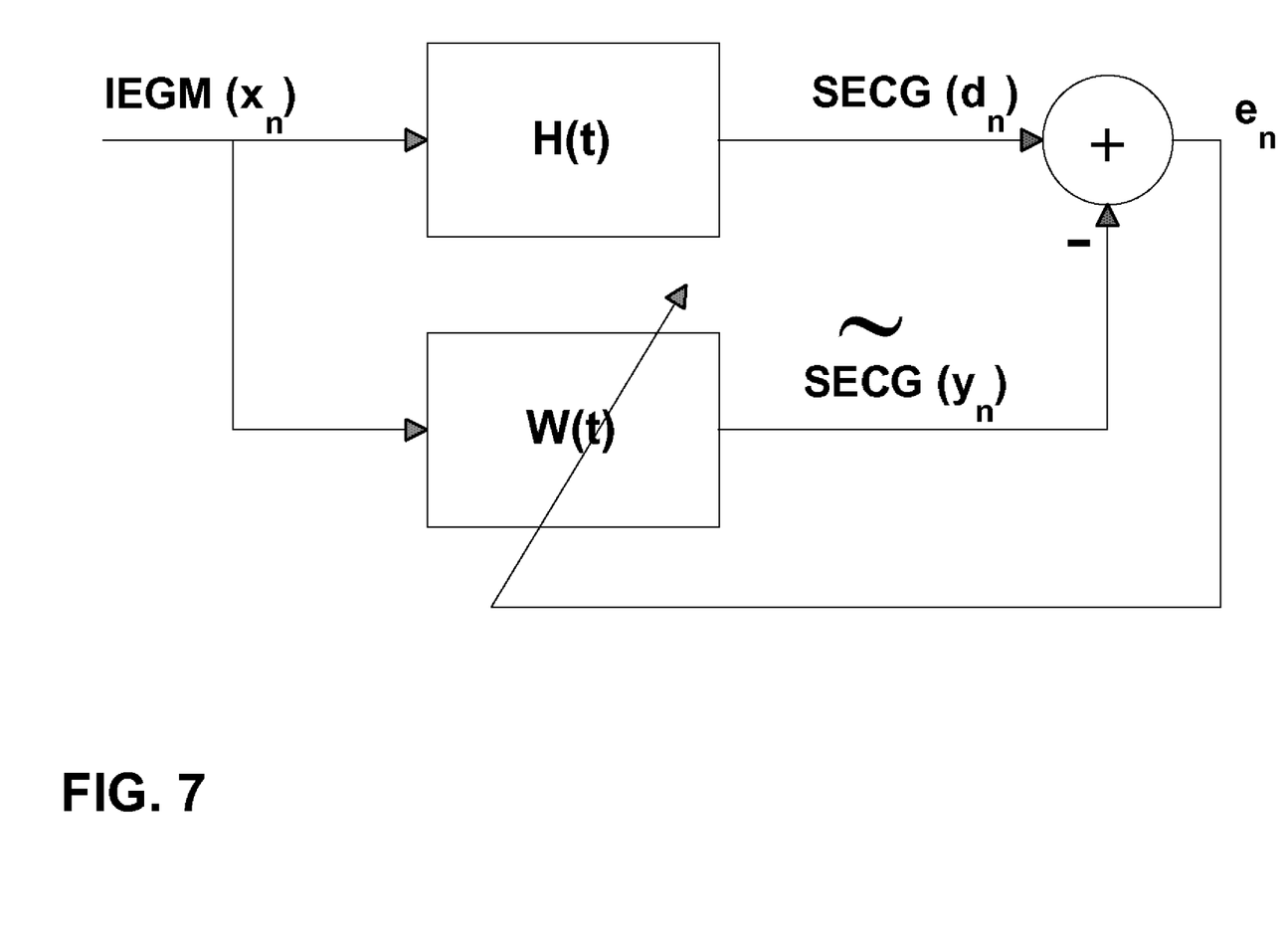
FIG. 7 shows the block diagram of the NLMS algorithm.

Refer to FIG. 7. In a preferred embodiment, the NLMS algorithm is chosen for filter characterization. The discrete input signal IEGM ($x_n$) and the corresponding output signal SECG ($d_n$) are assumed to be related by a transfer function H(t), whose filter characteristics are unknown. The NLMS algorithm aims to model this transfer function using a time-varying filter W(t), so that when given the same input ($x_n$), its output ($y_n$) best resembles the desired output ($d_n$). In other words, the NLMS algorithm adaptively adjusts the coefficients of the filters W(t), so that the error term ($e_n=d_n-y_n$) is minimized. The adaptation process can be described by the following equations:

$$y_n = W'_{n-1} \cdot x_n$$
$$e_n = d_n - y_n$$
$$W_n = \alpha \cdot W_{n-1} + \mu \cdot \frac{e_n \cdot x_n}{\varepsilon + x'_n \cdot x_n}$$

where α is the leakage factor ranging from 0 to 1, μ is the adaptation step size ranging from 0 to 2, ε is a small positive bias term that is used to improve the stability of the adaptation process. In a typical embodiment, for both atrial and ventricular channels, the filter length is set to 16 for sampling rate of 256 Hz and 32 for 512 Hz.

Figure 8:
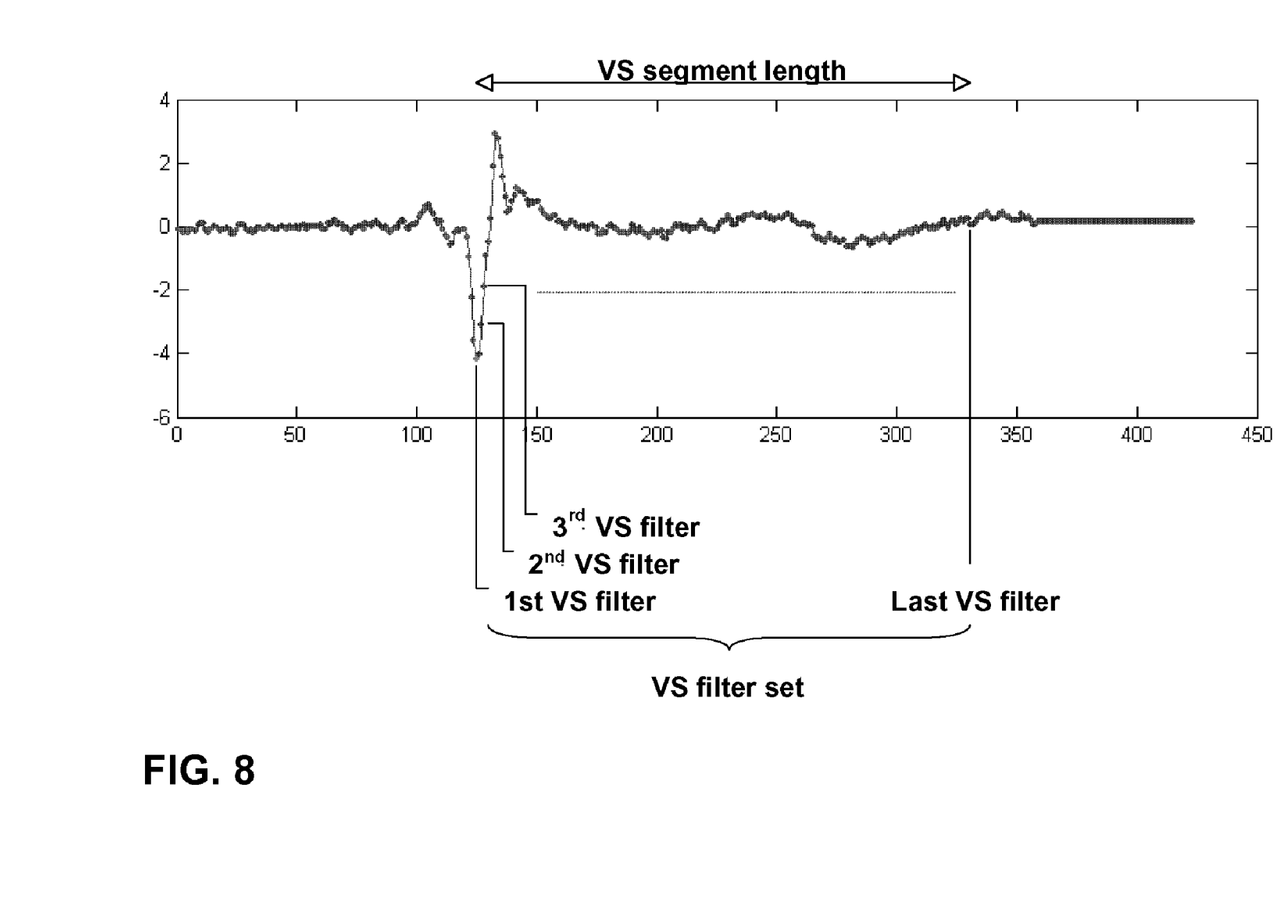
FIG. 8 illustrates the sample-wise filters aligned with the fiducial point.

For a stationary signal, the adapted NLMS filter is generally time-invariant. However, for non-stationary cardiac signal, after adaptation, the filter characteristics still varies from sample to sample within a cardiac cycle, particularly during the signal complexes. Therefore, in order to accurately estimate the SECG from the IEGM, it is necessary to apply sample-wise filters with proper segment length (number of samples) to the IEGM. That is, during the segment following the IEGM fiducial point, each sample is processed with a specific filter, as illustrated in FIG. 8.

In a preferred embodiment, the segment length is 100 ms for AS filters and 400 ms for VS filters to cover the P wave and QRS-T waves, respectively. For AP filters and VP filters, the segment length is preferably short (e.g., 40 ms) in order to apply sense filters for possible intrinsic events after non-capture paces. In another embodiment, the AP filters and VP filters have long segment lengths (e.g., 100 ms and 400 ms, respectively). A capture detection module (e.g., by analyzing the evoked potential) is activated after the pace. If capture is confirmed, then continue apply the pace filters. On the other hand, if non-capture is detected, then sense filters are applied.

It has been discovered by the inventors that, although the adapted atrial and ventricular filters show time-variant behaviour, the filter spectrum at the fiducial point (first sample) could be regarded as a rough approximation of the filter spectrum around the fiducial point (or during the signal complex). These observations led to the following considerations in designing filters for obtaining a Lead-free ECG:

1. There is no single fixed filter (or filter set) that could universally characterize the input-output relationship between IEGM and SECG. Optimal filters must be individually characterized based on representative IEGM/SECG templates.

2. If fiducial point is available (e.g., in the presence of an event marker signal), the sample-wise filters characterized from IEGM and SECG templates should be used to account for temporal variation of the frequency spectrum, in order to synthesize the SECG as accurately as possible. The first filter is aligned with respective IEGM fiducial point, the second filter is applied to the next sample, and so on, until the last filter (within the filter set) is applied to the last sample of the predefined segment, or when a new fiducial point is detected.

3. If fiducial point is not available (e.g., in the absence of event markers), or after the last filter (within the filter set) is applied to the IEGM sample (end of predefined segment following a previous fiducial point), the characterized filter at the fiducial point could be used to roughly estimate the SECG.

The optimal filters are the atrial and ventricular filters characterized by the NLMS algorithm based on the input IEGM and SECG templates. Applying these filters to the same IEGM templates and comparing the filtered output with the SECG templates can quantitatively assess the performance of these filters, for example, by using metric of correlation coefficient (CC) as defined below:

$$CC=(y-\bar{y})^T(d-\bar{d})/\|y\|\cdot\|d\|$$

Here, y and d respectively represent the vector of filtered output (filtered IEGM template) and desired output (SECG template), with respective mean values of $\bar{y}$ and $\bar{d}$. The CC is an index that measures the similarity between two vectors. The filters are optimal when CC approaches 1.

In a typical embodiment, the NLMS parameters are fixed: α=0.95, μ=1.0 and ε=1e-10 (for both atrial and ventricular channels). Alternatively, parameter a for each channel can be optimized by automatically looping through a range of values and searching for maximum CC. The ratio between peak amplitude of d and the peak amplitude of y is automatically determined as the gain factor during active filtering stage, so that the peak amplitude of the output ECG signal is similar to that of the SECG template.

Figure 9:
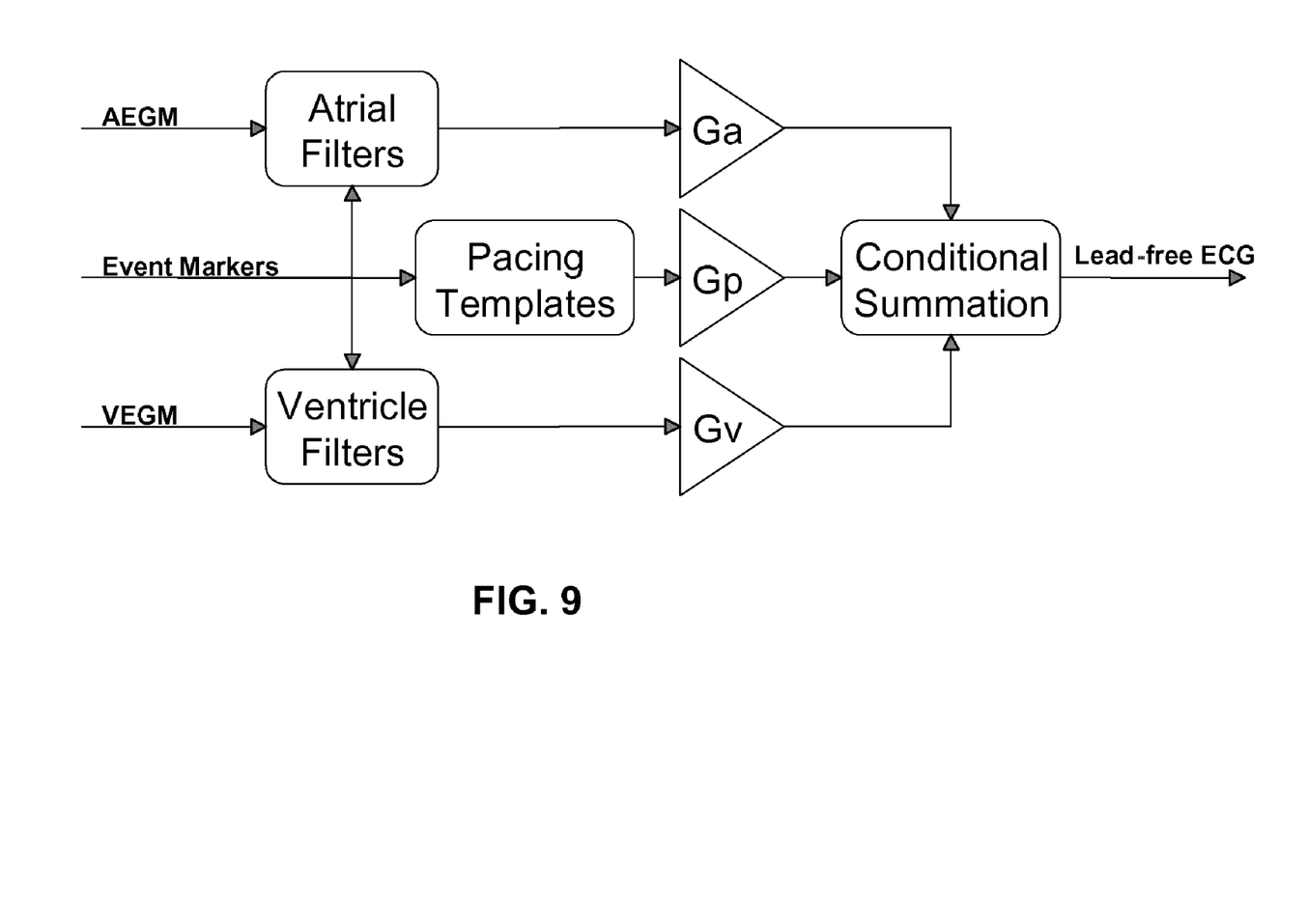
FIG. 9 shows the schematic block diagram of the active filtering stage.

Refer to FIG. 9. Once atrial and ventricular filters (for sensed and paced events) are characterized based on IEGM and SECG templates, these filters can be used to process the input IEGM and generate the output ECG (Lead-free ECG). In general, the input AEGM is actively filtered by the atrial filtering stage using the atrial filter coefficients, and the input VEGM is actively filtered by the ventricular filtering stage using the ventricle filter coefficients, all under control of the event markers provided by the implantable device 10.

Specifically,

Upon detection of the fiducial point following an atrial sense event, the first AS filter is applied to the AEGM sample at the fiducial point. Then the second AS filter is applied to the next AEGM sample, and so on, until the last AS filter (within the AS filter set) is applied to the last sample of the predefined atrial segment, or when a new fiducial point is detected. Meanwhile, for the ventricular channel, the first VS filter (corresponding to the VS fiducial point) is repeatedly applied to the VEGM samples.

Similarly, upon detection of the fiducial point following a ventricular sense event, the first VS filter is applied to the VEGM sample at the fiducial point. Then the second VS filter is applied to the next VEGM sample, and so on, until the last VS filter (within the VS filter set) is applied to the last sample of the predefined ventricle segment, or when a new fiducial point is detected. Meanwhile, for the atrial channel, the first AS filter (corresponding to the AS fiducial point) is repeatedly applied to the AEGM samples.

Upon delivery of an atrial stimulation pulse and thus, an atrial paced event, the first AP filter is applied to the AEGM sample corresponding to the AP marker. Then the second AP filter is applied to the next AEGM sample, and so on, until the last AP filter (within the AP filter set) is applied to the last sample of the predefined atrial segment, or when a new fiducial point is detected. Note that AEGM is considered free of pacing artifact due to pace blanking.

Similarly, upon delivery of a ventricular stimulation pulse and thus a ventricular pace event VP, the first VP filter is applied to the VEGM sample corresponding to the VP marker. Then the second VP filter is applied to the next VEGM sample, and so on, until the last VP filter (within the VP filter set) is applied to the last sample of the predefined ventricle segment, or when a new fiducial point is detected. Note that VEGM is considered free of pacing artifact due to pace blanking.

After the last filter (within the filter set) is applied to the IEGM sample (end of predefined segment following a previous fiducial point), the first AS filter (corresponding to AS fiducial point) is repeatedly applied to the AEGM samples, and the first VS filter (corresponding to VS fiducial point) is repeatedly applied to the VEGM samples.

The filtered AEGM and VEGM, together with the predefined pacing template, are respectively gained, and then conditionally summed to generate the output ECG signal (Lead-free ECG).

More specifically:

Following detection of AS fiducial point and within the predefined atrial segment, the output ECG signal is the sum of (a) the AEGM processed by the sample-wise AS filters, and (b) the VEGM processed by the first VS filter (corresponding to the VS fiducial point). The filtered AEGM will generally give a P-wave output, while concurrent ventricular activity (if any) may be reflected in the filtered VEGM component.

Following detection of VS fiducial point and within the predefined ventricle segment, the output ECG signal is the sum of (a) the VEGM processed by the sample-wise VS filters, and (b) the AEGM processed by the first AS filter (corresponding to the AS fiducial point). The filtered VEGM will generally give an output of QRS-T waves, while concurrent atrial activity (if any) may be reflected in the filtered AEGM component.

Following AP marker signal, a predefined AP pulse template is copied to the output to represent the pacing artifact. The output ECG signal is generated solely by the AEGM processed by the sample-wise AP filters (ventricle component is excluded to avoid far-field contribution), which will generally give a P-wave output if AP captures the atrium or near baseline if AP fails to capture.

Following a VP marker signal, a predefined VP pulse template is copied to the output to represent the pacing artifact. The output ECG signal is generated solely by the VEGM processed by the sample-wise VP filters (atrial component is excluded to avoid far-field contribution), which will generally give QRS-T wave output if VP captures the ventricle or near baseline if VP fails to capture.

After the last filter (in the filter set) is applied to the IEGM sample (end of predefined segment following a previous fiducial point), the output ECG signal is the sum of (a) the AEGM processed by the first AS filter (corresponding to the AS fiducial point), and (b) the VEGM processed by the first VS filter (corresponding to the VS fiducial point).

The atrial component and ventricular component can be independently adjusted by applying gain factors (user programmable or automatically determined during filter characterization stage as described above).

The AP and VP pulse templates are preferably stored in the external device 60 (e.g. a programmer or a remote service centre). The template width can be automatically adjusted to be proportional to the pacing pulse width. The template height can be automatically adjusted to be proportional to the pacing amplitude. In addition, the template height can be adjusted based on pacing polarity (e.g., smaller pulse amplitude for bipolar than unipolar pacing), and based on the SECG channel to be emulated.

Compared with fixed filter approach, the adaptive filter approach for generating an output ECG signal forming a Lead-free ECG corresponding to a SECG has the following advantages:

1. The atrial filters and ventricular filters can be independently optimized for each individual patient. Although the system characteristics vary from patient to patient due to difference in gender, age, body mass, torso geometry, etc., the adapted filters take these factors into consideration, and best characterize the system response that relates the IEGM to SECG.

2. The atrial filters and ventricular filters can be independently optimized for any specific IEGM lead configuration. Although the system input (IEGM) depends on the location and sensing characteristics of the endocardial lead, the adapted filters take theses factors into consideration (IEGM template), and consistently generate desired SECG output.

3. The atrial filters and ventricular filters can be independently optimized for any specific SECG lead. Although the system output (SECG) depends on the location of the surface lead, the adapted filters take these factors into consideration (SECG template), and consistently generate desired SECG output. Therefore, the adaptive filter approach can generate any type of SECG, including the standard 12-lead SECG.

Although an exemplary embodiment of the present invention has been shown and described, it should be apparent to those of ordinary skill that a number of changes and modifications to the invention may be made without departing from the spirit and scope of the invention. In particular, it is possible to implement and/or adapt the features of the claimed method and apparatus for deriving an SECG from an IEGM to different types of implantable medical devices such as dual-chamber (RA-RV), three-chamber (BiA-RV, or RA-BiV), or four-chamber (BiA-BiV) implantable cardiac devices including pacemakers, defibrillators and cardiovertors, which stimulate cardiac tissue electrically to control the patient's heart rhythm or different external devices such as programmers, patient devices etc. This invention can readily be adapted to such devices by following the present teachings. All such changes, modifications and alterations should therefore be recognized as falling within the scope of the present invention.

What is claimed is:

1. A system for heart monitoring comprising:
an intracardiac electrocardiogram IEGM input for an IEGM;
an active filtering stage, wherein said IEGM input is connected to said active filtering stage;
a filter characterization stage, wherein said active filtering stage is connected to said filter characterization stage;
wherein said filter characterization stage is configured to process a patient specific IEGM template that is recorded at least partially at a previous time and a corresponding surface electrocardiogram SECG template that was also recorded at least partially at said previous time wherein said filter characterization stage is configured to resample said SEGC template if necessary to ensure said SEGC template matches a sampling frequency of said IEGM template and remove direct current DC offset of said IEGM and SECG templates if said direct current DC offset exists in either of said IEGM and SECG templates and identify fiducial points of said IEGM and SECG templates to locate a P wave peak and an R wave peak and align a fiducial point in said IEGM with a corresponding fiducial point in said SECG at a programmable delay to account for phase delay between IEGM and SECG to match pairs of IEGM and SECG templates based on respective fiducial points and adjust said IEGM and SECG templates to have a same length;

wherein said filter characterization stage is further configured to adapt filter characteristics of said active filtering stage such that said filter characteristics best characterize an input-output relationship between said patient specific IEGM template and said corresponding SECG template; and, wherein said active filtering stage is configured to transform an incoming IEGM into an output electrocardiogram ECG signal, such that the output ECG signal closely resembles a morphology of a corresponding SECG as a consequence of adaptation of the filter characteristics by the filter characterization stage.

2. The system according to claim 1, wherein said filter characterization stage is configured to determine a difference between the SECG template and an output signal and to iteratively determine those filter characteristics that lead to least mean squares of said difference.

3. The system according to claim 1, wherein said filter characterization stage comprises a marker input for a marker signal and wherein said filter characterization stage is configured to determine said fiducial points based on said marker signal.

4. The system according to claim 1, wherein said active filtering stage comprises at least two individual filters, wherein each of said at least two individual filters comprises an individual set of filter coefficients.

5. The system according to claim 4, wherein said active filtering stage comprises an atrial sense event AS filter configured to filter atrial IEGM templates that correspond to an atrial sense event, an atrial pace event AP filter configured to filter said atrial IEGM templates that correspond to an atrial pace event, a ventricular sense event VS filter configured to filter ventricular IEGM templates that correspond to a ventricular sense event and a ventricular pace event VP filter configured to filter said ventricular IEGM templates that correspond to a ventricular pace event.

* * * * *